United States Patent
Diaz et al.

(10) Patent No.: US 6,811,561 B2
(45) Date of Patent: Nov. 2, 2004

(54) SMALL DIAMETER DEPLOYMENT SYSTEM WITH IMPROVED HEADPIECE

(75) Inventors: Roberto Diaz, Miami, FL (US); Robert Lulo, Pembroke Pines, FL (US); Brett E. Naglreiter, Hollywood, FL (US)

(73) Assignee: Cordis Neurovascular, Inc., Miami Lakes, FL (US)

( * ) Notice: Subject to any disclaimer, the term of this patent is extended or adjusted under 35 U.S.C. 154(b) by 414 days.

(21) Appl. No.: 10/095,317

(22) Filed: Mar. 11, 2002

(65) Prior Publication Data

US 2003/0093094 A1 May 15, 2003

Related U.S. Application Data

(60) Provisional application No. 60/335,938, filed on Nov. 15, 2001.

(51) Int. Cl.⁷ .............................................. A61M 29/00
(52) U.S. Cl. ..................... 606/200; 606/151; 604/104
(58) Field of Search ................. 606/200, 108, 606/151, 153; 604/104, 22, 508, 509; 600/585; 424/467; 623/1.11

(56) References Cited

U.S. PATENT DOCUMENTS

| | | | |
|---|---|---|---|
| 3,952,747 A | * | 4/1976 | Kimmell, Jr. ............... 606/200 |
| 5,108,407 A | | 4/1992 | Geremia et al. |
| 5,122,136 A | | 6/1992 | Guglielmi et al. |
| 5,217,484 A | * | 6/1993 | Marks ........................ 606/200 |
| 5,263,964 A | | 11/1993 | Purdy |
| 5,350,397 A | | 9/1994 | Palermo et al. |
| 5,382,259 A | | 1/1995 | Phelps et al. |
| 5,853,418 A | | 12/1998 | Ken et al. |
| 5,895,391 A | | 4/1999 | Farnholtz |
| 6,179,857 B1 | | 1/2000 | Diaz et al. |
| 6,183,491 B1 | | 2/2000 | Lulo |
| 6,379,374 B1 | | 4/2000 | Hieshima et al. |
| 6,063,100 A | | 5/2000 | Diaz et al. |
| 6,068,644 A | | 5/2000 | Lulo et al. |
| 6,102,933 A | | 8/2000 | Lee et al. |
| 6,113,622 A | | 9/2000 | Hieshima |
| 6,514,264 B1 | * | 2/2003 | Naglreiter ................... 606/151 |
| 6,544,225 B1 | * | 4/2003 | Lulo et al. ................... 604/104 |
| 6,607,541 B1 | * | 8/2003 | Gardiner et al. ............ 606/151 |

OTHER PUBLICATIONS

Instructions For Use, entitled "Trufill 3D Detachable Coil System," Document #635GS082, Revision 1, by Cordis Endovascular Systems, Inc.

* cited by examiner

Primary Examiner—Julian W. Woo

(57) ABSTRACT

A medical apparatus for placing an embolic coil at a preselected position within a vessel comprising a coil assembly having an embolic coil attached to a cylindrical headpiece having at least one bending point formed by a circumferential groove and a deployment catheter having a distal section for retaining the coil assembly such that, when the deployment catheter is pressurized with a fluid the distal section of the catheter expands radially to release the coil assembly at the preselected position.

8 Claims, 2 Drawing Sheets

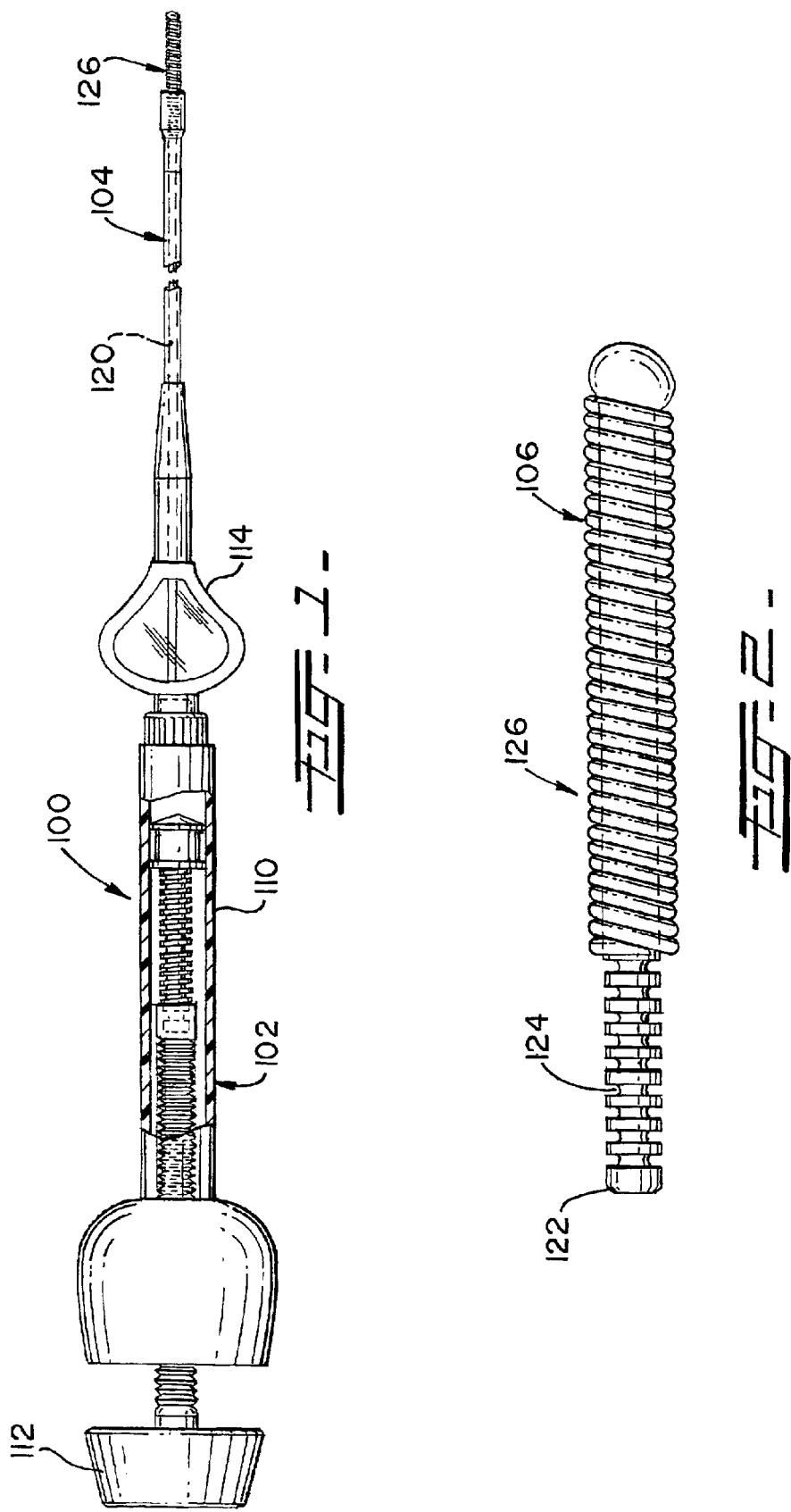

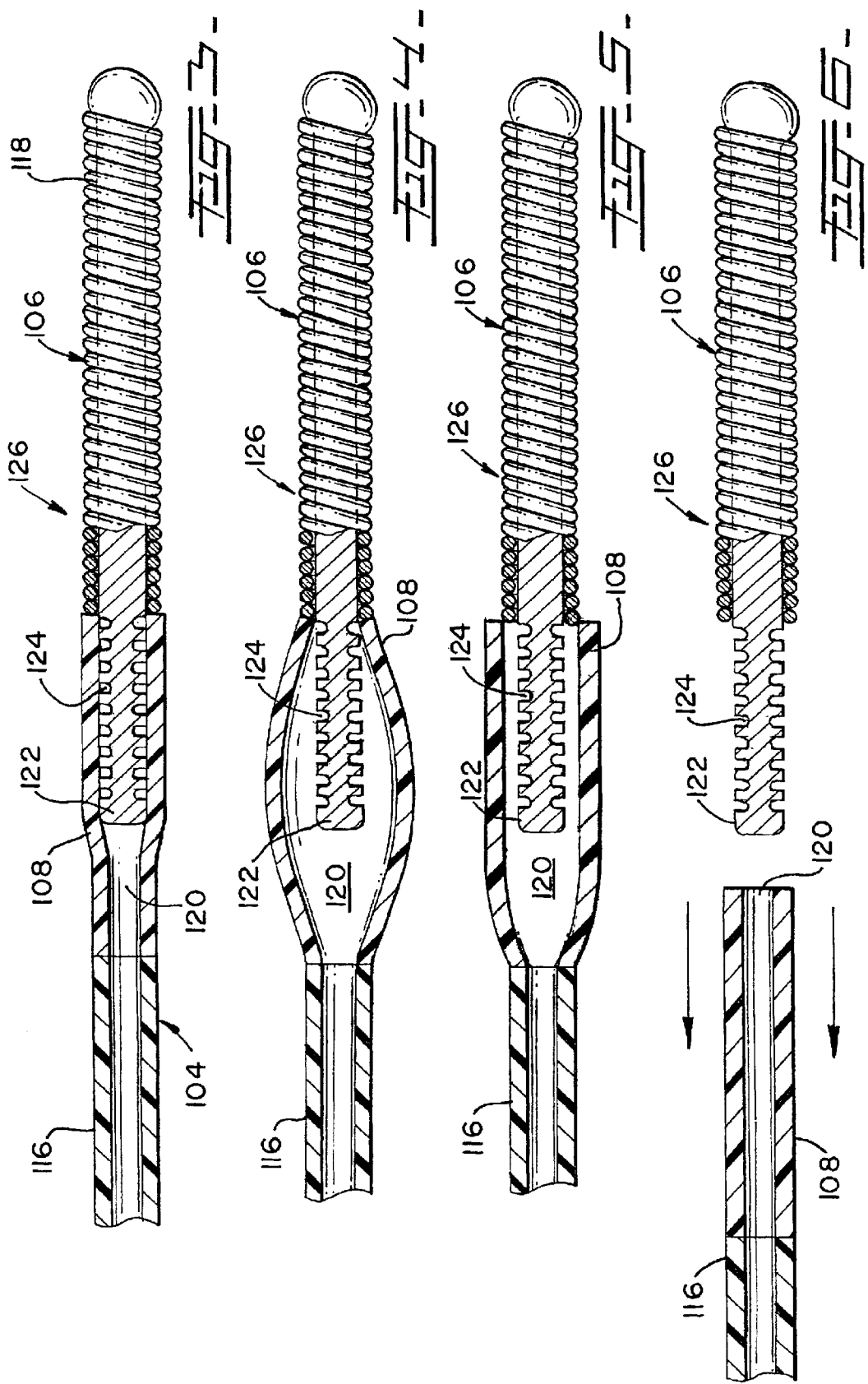

SMALL DIAMETER DEPLOYMENT SYSTEM WITH IMPROVED HEADPIECE

This patent application claims the benefit of provisional patent application Ser. No. 60/335,938 filed on Nov. 15, 2001.

BACKGROUND OF THE INVENTION

1. Field of the Invention

This invention relates to a medical apparatus for placing a coil assembly at a preselected position within a vessel of the human body, and more particularly, relates to a deployment catheter having a distal section for retaining and transporting the coil assembly within the vessel and having a control mechanism for releasing the coil assembly at the preselected position. This apparatus is particularly suited for transporting the coil assembly through the tortuous vasculature of the human brain and releasing the coil assembly within an aneurysm.

2. Description of the Prior Art

For many years physicians have been placing various devices within a blood vessel of the human body in order to treat an aneurysm or to occlude a vessel. Such devices are placed within the aneurysm or vessel using one of several catheter deployment systems. These deployment systems transport and release devices at a particular location within the vessel. The combination of different devices and deployment systems provide physicians with reliable methods of treating aneurysms.

Various types of devices are placed within an aneurysm or a vessel to occlude the flow of blood by promoting thrombus formation. Such devices include dilatation balloons, radiopaque fluids, liquid medications, and embolic coils. Embolic coils may take the form of helically wound coils, randomly wound coils, coils wound within other coils, or many other coil configurations. These coils are generally formed of radiopaque metallic materials, such as platinum, gold, and tungsten, or alloys of these metals. Often times, several coils are placed at a given location in order to occlude the flow of blood through the vessel.

One example of an embolic coil design is disclosed in U.S. Pat. No. 6,179,857 entitled, "Stretch Resistant Embolic Coil with Variable Stiffness." The coil is a helically wound coil in which various combinations of adjacent turns are spot welded together to create a stretch resistant coil of a preselected flexibility. Another coil configuration is disclosed in U.S. Pat. No. 6,183,491 entitled, "Embolic Coil Deployment System with Improved Embolic Coil" which shows an embolic coil having a relatively flexible proximal portion which resists stretching.

Also, U.S. Pat. No. 5,853,418 entitled "Stretch Resistant Vaso-occlusive Coils," discloses a helically wound coil having a polymeric stretch resistant member extending through the lumen of the coil and fixedly attached to both the distal end and the proximal end of the coil. Other examples of coil configurations are disclosed in U.S. Pat. No. 5,334, 210, entitled, "Vascular Occlusion Assembly" and U.S. Pat. No. 5,382,259 entitled, "Vaso-occlusion Coil With Attached Tubular Woven Or Braided Fibrous Coverings". With all coil designs, it is important that embolic coils remain very flexible for traveling through vessels when used with catheter deployment systems.

A variety of deployment systems are available for placing embolic coils within an aneurysm or vessel. An example of such a system is disclosed in U.S. Pat. No. 6,113,622 entitled, "Embolic Coil Hydraulic Deployment System," assigned to the same assignee as the present patent application. The hydraulic embolic coil deployment system uses fluid pressure which is applied to the lumen of the deployment catheter for expanding the distal section radially to release the embolic coil at a preselected position.

Another coil deployment system utilizes a deployment catheter having a socket at the distal end for retaining a ball which is bonded to the proximal end of the coil. The ball is placed in the socket within the lumen at the distal end of the deployment catheter, and the deployment system is then moved into a vessel to place the coil at a desired position. Then, a pusher wire with a piston at the end is pushed distally from the proximal end of the deployment catheter to thereby push the ball out of the socket and release the coil at the desired position. This system is disclosed in U.S. Pat. No. 5,350,397 entitled, "Axially Detachable Embolic Coil Assembly."

Also, U.S. Pat. No. 5,263,964 entitled, "Coaxial Traction Detachment Apparatus and Method" discloses another coil deployment system. This system uses glue or solder for attaching an embolic coil to a guidewire which is, in turn, placed within a flexible deployment catheter for positioning the coil within the vessel at a preselected position. Once the coil is at the desired position, the coil is restrained by the deployment catheter, and the guidewire is pulled from the proximal end of the deployment catheter causing the coil to be detached from the guidewire and released from the deployment system.

Additionally, a small diameter vasoocclusive coil deployment system is disclosed in U.S. patent application Ser. No. 09/580,684 entitled, "Small Diameter Embolic Coil Hydraulic Deployment System," filed on May 30, 2000 and assigned to the same assignee as the present patent application. In this system, the distal end of a cylindrical headpiece is inserted into and bonded with an embolic coil. The proximal end of the cylindrical headpiece has a diameter approximately equal to the diameter of a lumen of a deployment catheter allowing the proximal end of the cylindrical headpiece to be disposed in fluid-tight engagement within the lumen of the distal section of the deployment catheter. When fluid pressure is applied to the lumen of the deployment catheter, the wall of the distal section of the deployment catheter expands radially and releases the cylindrical headpiece along with the embolic coil.

Examples of other deployment systems are disclosed in U.S. Pat. No. 5,122,136 entitled, "Endovascular Electrolytically Detachable Guidewire Tip For The Electroformation Of Thrombus In Arteries, Veins, Aneurysms, Vascular Malformations And Arteriovenous Fistulas" and U.S. Pat. No. 5,108,407 entitled, "Method And Apparatus For Placement Of An Embolic Coil."

SUMMARY OF THE INVENTION

In accordance with one aspect of the present invention, a small diameter deployment system is provided for placing a coil assembly at a preselected position within a vessel of the body. The deployment system includes an elongated deployment catheter formed of a material which is sufficiently flexible to pass through the vasculature of the body. The proximal section of the catheter has substantially no radial expansion when fluid pressure is applied to the lumen of the catheter. The distal section of the catheter expands radially when fluid pressure is applied. The deployment system also includes a coil assembly which includes a flexible embolic coil and a cylindrical headpiece disposed within the embolic coil. The headpiece has at least one bending point formed by a circumferential groove, and the headpiece is disposed in fluid-tight engagement within the lumen of the catheter. Finally, the deployment system includes a connector coupled to the proximal section of the catheter. The connector is adapted for a fluid pressure generating device used for applying fluid pressure to the lumen of the catheter causing the distal section of the catheter to expand radially thereby releasing the headpiece and deploying the coil assembly.

In accordance with another aspect of the present invention, a small diameter deployment system is provided for placing an agent assembly at a preselected position within a vessel of the body. The deployment system includes an elongated deployment catheter formed of a material which is sufficiently flexible to pass through the vasculature of the body. The proximal section of the catheter has substantially no radial expansion when fluid pressure is applied to the lumen of the catheter. The distal section of the catheter expands radially when fluid pressure is applied. The deployment system also includes an agent assembly which includes a medical agent attached to a cylindrical headpiece. The headpiece has at least one bending point formed by a circumferential groove, and the headpiece is disposed in fluid-tight engagement within the lumen of the catheter. Finally, the deployment system includes a connector coupled to the proximal section of the catheter. The connector is adapted for a fluid pressure generating device used for applying fluid pressure to the lumen of the catheter causing the distal section of the catheter to expand radially thereby releasing the headpiece and deploying the agent assembly.

In accordance with another aspect of the present invention, a small diameter deployment system is provided for placing a device assembly at a preselected position within a vessel of the body. The deployment system includes an elongated deployment catheter formed of a material which is sufficiently flexible to pass through the vasculature of the body. The proximal section of the catheter has substantially no radial expansion when fluid pressure is applied to the lumen of the catheter. The distal section of the catheter expands radially when fluid pressure is applied. The deployment system also includes a device assembly which includes a medical device attached to a cylindrical headpiece. The headpiece has at least one bending point formed by a circumferential groove, and the headpiece is disposed in fluid-tight engagement within the lumen of the catheter. Finally, the deployment system includes a connector coupled to the proximal section of the catheter. The connector is adapted for a fluid pressure generating device used for applying fluid pressure to the lumen of the catheter causing the distal section of the catheter to expand radially thereby releasing the headpiece and deploying the device assembly.

In accordance with another aspect of the present invention, a coil assembly is provided for occluding the flow of blood at a preselected position within a vessel. The coil assembly includes a flexible embolic coil and a cylindrical headpiece disposed within the embolic coil. The headpiece has at least one bending point formed by a circumferential groove.

In accordance with another aspect of the present invention, an agent assembly is provided for occluding the flow of blood at a preselected position within a vessel. The agent assembly includes a medical agent attached to a cylindrical headpiece. The headpiece has at least one bending point formed by a circumferential groove.

In accordance with another aspect of the present invention, a device assembly is provided for occluding the flow of blood at a preselected position within a vessel. The device assembly includes a medical device attached to a cylindrical headpiece. The headpiece has at least one bending point formed by a circumferential groove.

In accordance with a similar aspect of the present invention, the cylindrical headpiece takes the form of a headpiece with four bending points formed by circumferential grooves.

In accordance with a similar aspect of the present invention, the cylindrical headpiece takes the form of a headpiece with nine bending points formed by circumferential grooves.

In accordance with a similar aspect of the present invention, the flexible embolic coil, medical agent, and medical device have an outside diameter which is approximately equal to the outside diameter of the deployment catheter to thereby provide a deployment system of a uniform outside diameter.

In accordance with a similar aspect of the present invention, the deployment system includes a syringe coupled to the connector and used for applying fluid pressure to the lumen of the catheter causing the distal section of the catheter to expand radially thereby releasing the headpiece.

These aspects of the invention and the advantages thereof will be more clearly understood from the following description and drawings of the preferred embodiment.

BRIEF DESCRIPTION OF THE DRAWINGS

FIG. 1 is an enlarged, partially sectioned view of a small diameter deployment system with a coil assembly;

FIG. 2 is an enlarged view showing the coil assembly with a cylindrical headpiece with nine bending points formed by circumferential grooves and an embolic coil attached to the headpiece;

FIG. 3 is an enlarged, partially sectioned view of the coil assembly disposed in the distal section of a deployment catheter of the deployment system;

FIG. 4 is an enlarged, partially sectioned view showing radial expansion of the distal section of the deployment catheter;

FIG. 5 is an enlarged, partially sectioned view of the distal section of the deployment catheter releasing the coil assembly; and, FIG. 6 is an enlarged, partially sectioned view showing the distal section of the deployment catheter after releasing the coil assembly.

DESCRIPTION OF THE PREFERRED EMBODIMENT

FIG. 1 illustrates a small diameter deployment system 100 which includes a syringe 102 coupled to the proximal end of a deployment catheter 104. The syringe 102 includes a threaded piston 110 which is controlled by a handle 112 for infusing fluid into a lumen 120 of the deployment catheter 104. A coil assembly 126 is disposed within the lumen 120 of the distal section 108 of the deployment catheter 104. Also, the deployment catheter 104 includes a winged hub 114 which aides in the insertion of the deployment catheter 104 into the vascular system of the body.

FIG. 2 illustrates a coil assembly 126 which includes an embolic coil 106 and a cylindrical headpiece 122 with nine bending points formed by circumferential grooves 124. The length of the cylindrical headpiece 122 can range from 0.060 inches to 0.070 inches with a preferred length of 0.062 inches. Preferably, the circumferential grooves 124 are approximately 0.003 inches in width, approximately 0.002 inches in depth, and spaced about 0.003 inches apart from each other. The embolic coil 106 may take various forms and configurations and may even take the form of a randomly wound coil, however, a helically wound flexible embolic coil 106 is illustrated in FIG. 2. The embolic coil 106 is tightly wrapped and bonded to the cylindrical headpiece 122. Where the coil is bonded to the headpiece 122, adjacent turns of the embolic coil 106 are preferably continuously welded together and are in turn welded to the cylindrical headpiece 122 to provide a generally unitary structure. The cylindrical headpiece 122 has an outside diameter of about 0.008 inches which is approximately equal to the diameter of the lumen 120 of the deployment catheter 104. Preferably, the cylindrical headpiece 122 may be manufactured of platinum but can also be made of other materials, like alloys or plastics. With this construction, the cylindrical headpiece 122 is stiff enough to be deployed with the deployment system 100 yet flexible enough to transverse the vasculature of the human body.

FIG. 3 illustrates the deployment catheter 104 with the coil assembly 126 during transportation through the vessel. The cylindrical headpiece 122 is tightly held within the lumen 120 of the distal section 108 deployment catheter 104. In this position, the cylindrical headpiece 122 serves to provide a fluid-tight seal at the distal section 108 of the deployment catheter 104. The cylindrical headpiece 122 is disposed in the embolic coil 106 and serves to prevent the flow of fluid through the lumen 118 of the embolic coil 106. Most importantly, the diameter of the cylindrical headpiece 122 is approximately equal to or slightly larger than the diameter of the lumen 120 of the deployment catheter 104 so that, when the cylindrical headpiece 122 is inserted into the distal section 108 of the deployment catheter 104, the outside diameter of the embolic coil 106 is approximately equal to the outside diameter of the deployment catheter 104. This construction results in a deployment system 100 with an embolic coil 106 having an overall outside diameter approximately equal to that of the deployment catheter 104.

Preferably, the proximal section 116 of the deployment catheter 104 is formed of Pebax material having a durometer in a range of about 62D to 75D. The proximal section 116 is sufficiently flexible to transverse the vasculature of the human body, but is sufficiently rigid such that, when fluid pressure of approximately 90 to 450 psi is applied to the lumen 120 of the deployment catheter 104 there is very little, if any, radial expansion of the wall of the proximal section 116. The distal section 108 of the deployment catheter 104 is preferably formed of polymer material with a relatively low durometer which exhibits the characteristic that, when fluid pressure of approximately 90 to 450 psi is applied to the lumen 120 of the deployment catheter 104 the wall of the distal section 108 expands radially thereby releasing the cylindrical headpiece 122. The distal section 108 of the deployment catheter 104 is preferably formed of Pebax material having a durometer of between 25D and 55D with a durometer of 40D being the preferred durometer.

FIGS. 4 and 5 illustrate the deployment system 100 in action to release the coil assembly 126. More particularly, as shown in FIG. 3, when fluid pressure is applied to the lumen 120 of the deployment catheter 104 the relatively low durometer distal section 108 of the deployment catheter 104 begins to expand radially. As the distal section 108 continues to expand radially there comes a point, as illustrated in FIG. 4, in which the cylindrical headpiece 122 becomes disengaged from the lumen 120 of the distal section 108 of the deployment catheter 104 and the coil assembly 126 becomes released within the vessel.

As illustrated in FIG. 6, when the coil assembly 126 has been released from the deployment catheter 104, the deployment catheter 104 may be withdrawn, leaving the cylindrical headpiece 122 and embolic coil 106 positioned at the preselected location.

A novel system has been disclosed in which a cylindrical headpiece and an embolic coil are delivered precisely to a preselected position within a vessel. Although a preferred embodiment of the invention has been described, it is to be understood that various modifications may be made by those skilled in the art without departing from the scope of the present invention. For example, there are many variations and modifications of the embolic coil, including numerous coil winding configurations, or alternatively, other types of implant devices, such as a vascular filter.

Also, there are variations to the syringe used for applying fluid pressure to the lumen of the deployment catheter, including other fluid pressure generating devices used for increasing the pressure within the lumen of the deployment catheter in order to cause the distal section of the deployment catheter to expand radially.

In another alternative construction, the cylindrical headpiece may take on various configurations. One such configuration is a cylindrical headpiece with four bending points formed by circumferential grooves. The cylindrical headpiece may have a length of approximately 0.060 inches. The circumferential grooves may be 0.001 inches in width, 0.002 inches in depth, and approximately 0.003 inches apart from each other. The cylindrical headpiece may have an outside diameter of about 0.008 inches which is approximately equal to the diameter of the lumen of the deployment catheter 104. This construction results in a deployment system with an embolic coil having an overall outside diameter approximately equal to that of the deployment catheter.

Furthermore, the cylindrical headpiece may be coated with a flexible material, like a polymer, to create a smooth surface and equal diameter along the length of the headpiece. In this construction, the cylindrical headpiece acts as a plug to allow for proper hydraulic deployment while still allowing flexibility for transportation through the vasculature of the human body.

These and other modifications would be apparent to those having ordinary skill in the art to which this invention relates and are intended to be within the scope of the claims which follow.

That which is claimed is:

1. A small diameter deployment system for placing a coil assembly at a preselected position within a vessel, said deployment system comprising:

an elongated flexible deployment catheter having a small diameter lumen extending therethrough and having a proximal section and a distal section, said catheter being formed of a material which is sufficiently flexible to pass through the vasculature of the body, the proximal section of said catheter exhibiting the characteristic of having substantially no radial expansion when fluid pressure is applied to the lumen of said catheter, and the distal section of said catheter exhibiting the characteristic that, when fluid pressure is applied to the lumen of said catheter the wall of the distal section of said catheter expands radially;

a coil assembly comprised of a flexible embolic coil having a lumen extending therethrough and a cylindrical headpiece being disposed within the lumen of said embolic coil, said headpiece having at least one bending point comprised of a circumferential groove, and said headpiece having an outside diameter approximately equal to the diameter of the lumen of said catheter and being disposed in fluid-tight engagement within the lumen of said catheter; and, a connector coupled to the proximal section of said catheter and adapted for a fluid pressure generating device used for applying fluid pressure to the lumen of said catheter causing the distal section of said catheter to expand radially thereby releasing said headpiece and deploying said coil assembly.

2. A deployment system as defined in claim 1, wherein said headpiece has four bending points comprised of circumferential grooves.

3. A deployment system as defined in claim 1, wherein said headpiece has nine bending points comprised of circumferential grooves.

4. A deployment system as defined in claim 1, wherein said embolic coil has an outside diameter which is approximately equal to the outside diameter of the catheter to thereby provide a deployment system of a uniform outside diameter.

5. A deployment system as defined in claim 1, wherein said deployment system includes a syringe coupled to said connector used for applying fluid pressure to the lumen of said catheter causing the distal section of said catheter to expand radially thereby releasing said headpiece and deploying said coil assembly.

6. A coil assembly for occluding the flow of blood at a preselected position within a vessel, said coil assembly comprising:

a flexible embolic coil having a lumen extending therethrough; and, a cylindrical headpiece being disposed within the lumen of said embolic coil, and said headpiece having at least one bending point comprised of a circumferential groove.

7. A coil assembly as defined in claim 6, wherein said headpiece has four bending points comprised of circumferential grooves.

8. A coil assembly as defined in claim 6, wherein said headpiece has nine bending points comprised of circumferential grooves.

* * * * *